(12) United States Patent
Lindh et al.

(10) Patent No.: US 7,766,851 B2
(45) Date of Patent: Aug. 3, 2010

(54) BELOW KNEE ORTHOSIS

(75) Inventors: Kjell Lindh, Lidingö (SE); Leif Lindh, Täby (SE)

(73) Assignee: Centri AB (SE)

( * ) Notice: Subject to any disclaimer, the term of this patent is extended or adjusted under 35 U.S.C. 154(b) by 35 days.

(21) Appl. No.: 12/282,388

(22) PCT Filed: Mar. 13, 2007

(86) PCT No.: PCT/SE2007/000237

§ 371 (c)(1),
(2), (4) Date: Sep. 10, 2008

(87) PCT Pub. No.: WO2007/106017

PCT Pub. Date: Sep. 20, 2007

(65) Prior Publication Data

US 2009/0037001 A1    Feb. 5, 2009

(30) Foreign Application Priority Data

Mar. 14, 2006    (SE) .................................. 0600559

(51) Int. Cl.
*A61F 5/00*    (2006.01)
(52) U.S. Cl. ............................... 602/28; 602/16; 602/27

(58) Field of Classification Search .................. 623/52, 623/55; 602/16, 23, 28, 29, 62, 27
See application file for complete search history.

(56) References Cited

U.S. PATENT DOCUMENTS 2,949,111 A * 8/1960 Ruotoistenmaki ............. 602/28
7,270,644 B2 * 9/2007 Ingimundarson ............. 602/27

FOREIGN PATENT DOCUMENTS

| GB | 117877 A | 10/1918 |
| WO | WO 01/68010 A2 | 9/2001 |
| WO | WO 2005/097014 A1 | 10/2005 |

OTHER PUBLICATIONS

International Search Report dated Jun. 25, 2007, issued in corresponding international application No. PCT/SE2007/000237.

* cited by examiner

*Primary Examiner*—Bruce E Snow
(74) *Attorney, Agent, or Firm*—Ostrolenk Faber LLP

(57) ABSTRACT

A below-knee orthosis comprises a footplate, which is carried by a connecting element projecting therefrom, the upper end part of which has a releasable coupling that can be coupled to an upper part of a patient's lower leg, a longitudinal section of the connecting element being formed of a spring element, which extends in a curved path at a radial distance from a fulcrum of the spring element, and said fulcrum being placed to be essentially aligned with the patient's ankle-joint axis.

5 Claims, 2 Drawing Sheets

BELOW KNEE ORTHOSIS

CROSS REFERENCE TO RELATED APPLICATIONS

The present application is a 35 U.S.C. §371 National Phase conversion of PCT/SE2007/000237, filed Mar. 13, 2007, which claims benefit of Swedish Application No. 0600559-9, filed Mar. 14, 2006, the disclosure of which is incorporated herein by reference. The PCT International Application was published in the English language.

The invention relates to a below-knee orthosis of the kind that is seen in the preamble of the appended claim 1.

Orthoses of the kind defined in the preamble of claim 1 are already known from practice, and find use for patients having "drop foot", which means that the foot-blade lifting ability of the patient entirely or partly has ceased, while the patient has left at least some ability to turn down the foot by means of muscles on the back side of the lower leg. In the absence of an orthosis, such a state of ill-health is particularly troublesome during walking, since the patient then has to lift the lower leg/knee so high that the toes of the pendent foot do not drag on the ground upon a step forward. The drop foot may arise as a consequence of a stroke in the patient.

A previously known below-knee orthosis comprises a footplate, which is carried by a connecting element projecting therefrom, the upper end part of which element can be coupled to the upper part of the lower leg with a releasable coupling. The foot of the patient is inserted together with the footplate into a shoe, and the front and rear parts of the footplate may be flexible to allow an elastic deflection of the front and rear parts of the footplate in spite of the footplate having a stiff connection to the connecting element. A problem is then that the deflection motions of the footplate take place around axes that are at substantial distance from the ankle joint. Another below-knee orthosis already known from practice comprises a pivot joint fitted in the connecting element and spring-loaded against the normal position of the foot, the axis of the pivot joint essentially being aligned with the ankle joint. Such a pivot joint having two mutually rotationally mounted parts mutually biased against a normal position via a spring device, and that is placed in axial alignment with and outside the adjacent projecting ankle joint ball of the ankle, is inappropriate for several reasons, for instance, that the pivot joint then becomes particularly bulky, just because it is placed outside the laterally projecting ankle-joint button, and further as a consequence of the fact that there should be a certain distance between the pivot joint and the button of the ankle joint to allow a turning of the foot/foot sole/orthosis footplate laterally without interference arising between the pivot joint and the ankle-joint button.

The problem is accentuated by the fact that the patient often, as far as possible, wants to conceal his or her disablement and therefore desires, as far as possible, to let the connecting element and a possible pivot joint be situated close to the lower leg, for instance under a sock. This circumstance may be a reason for orthosis manufacturers rather having selected to make the below-knee orthosis without any pivot joint in the connecting element in alignment with the ankle joint, and have further let the connecting element be stiffly connected to the footplate, which instead has been made deflectable in the front and rear parts thereof, in the forward-rearward direction of the foot.

Therefore, an object of the invention is to provide a below-knee orthosis, the connecting part of which can extend quite close to the side of the lower leg and foot, but still allow a swinging motion of the footplate around an axis that essentially coincides with the axis of the ankle joint, spring members being provided to afford a return motion in the plane of the swinging motion of the foot toward a normal position, i.e., a position in which the footplate carries the underside of the foot substantially perpendicularly to the axis of the lower leg.

In that connection, an additional object is to produce a springing function that affords a weaker characteristic for the swinging up of the footplate from the neutral position, than for the swinging down of the footplate from the neutral position.

The object is entirely or partly attained by the invention.

The invention is defined in the appended claim 1.

Embodiments of the invention are defined in the appended dependent claims.

In the following, the invention will be described in the form of examples, reference being made to the appended drawing.

Figure 1:
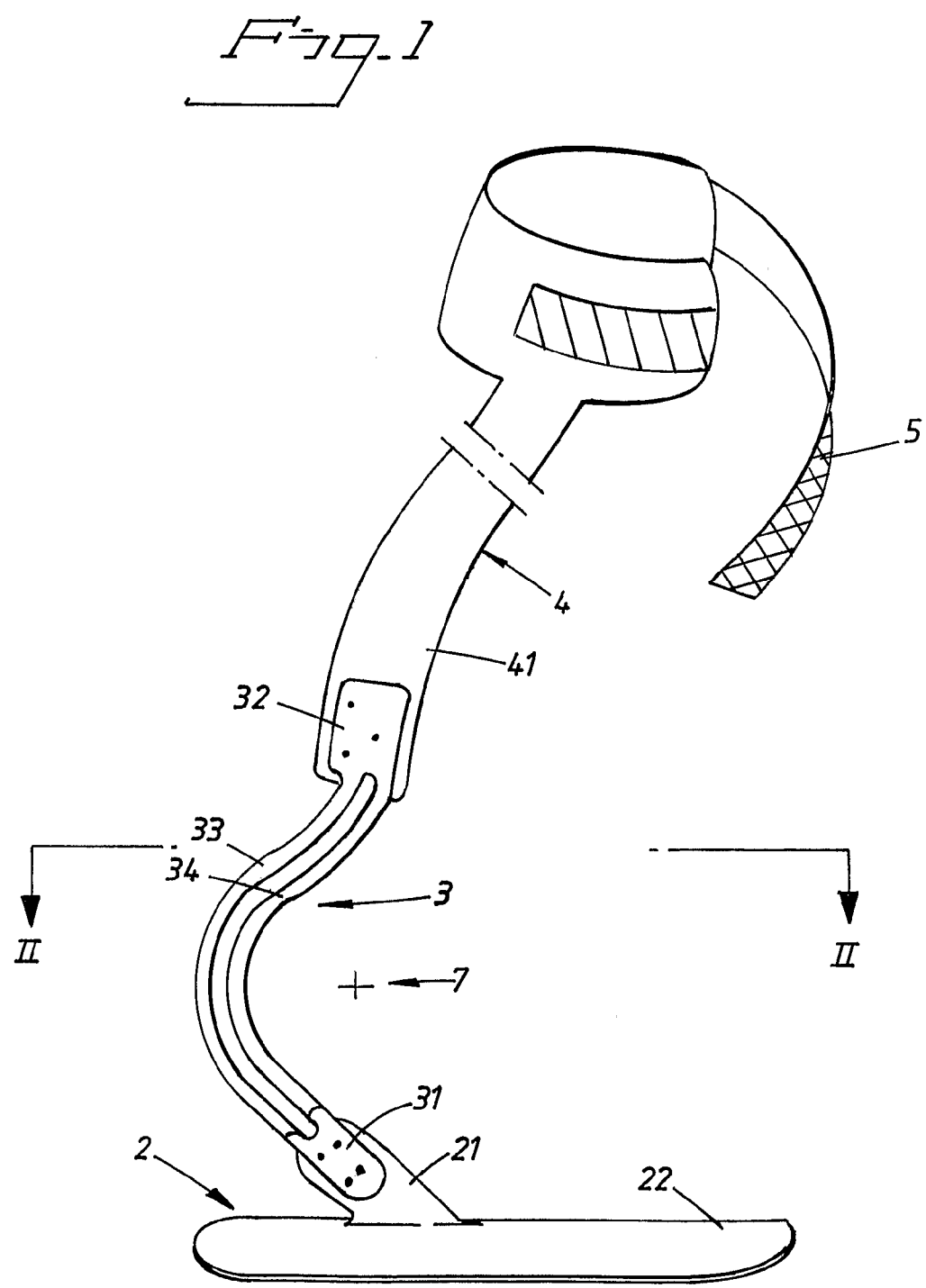
FIG. 1 shows a side view of a below-knee orthosis.

In the drawing, a below-knee orthosis is shown, which comprises a thin footplate 2, which forms a support for the underside of the foot of the patient. The footplate is shown to have an upwardly and rearwardly directed tongue 21 connecting to the inner edge, which tongue extends at a substantially right angle to the footplate 2. Furthermore, a spring 3 is shown, which with a lower end portion 31 is fixedly connected to the tongue 21. The upper end portion 32 of the spring is fixedly connected to a lower end part 41 of a substantially flat rail 41, which extends essentially in the same plane as the tongue 21. The upper end portion of the rail 4 is shown to be U-shaped as viewed in a plane parallel to the plane of the footplate 2, the opening of the U-shaped portion being shown facing forward in order to receive the rear part of the lower leg, i.e., the upper portion on the calf muscles of the lower leg. A retaining strap is shown to extend between the free branch ends of the U-shaped portion in order to surround and enclose the lower leg. The strap 5 may be connected to the outside of the branches by means of Velcro couplings, at least to one of the branches.

A patient's foot that is supported on the footplate 2 has an ankle-joint axis 7, which essentially is perpendicular to the longitudinal direction of the footplate 2 and parallel to the extension plane of the footplate 2. In FIG. 1, it is seen that the spring 3 extends along a curved path between the end portions 32 thereof, the spring extending at a distance from the joint axis 7 in order not to interfere with the protuberance 6 of the ankle joint.

Figure 2:
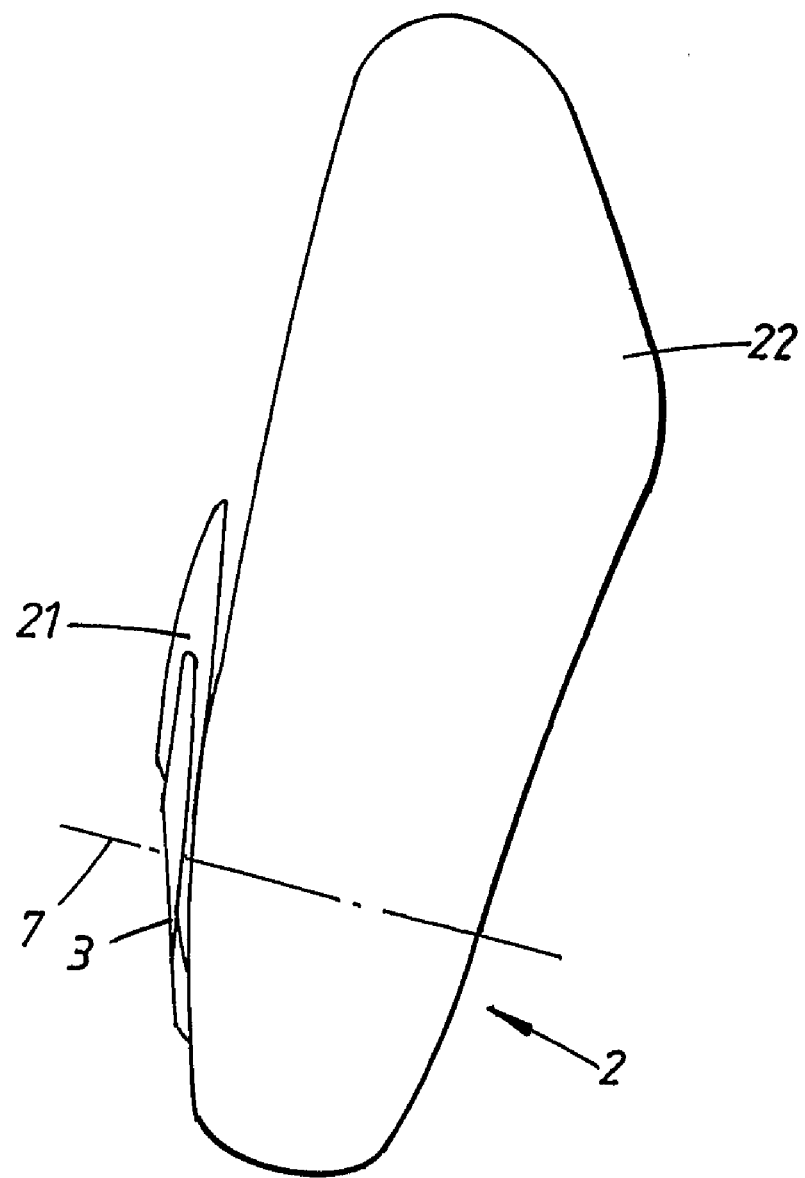
FIG. 2 shows a schematic view taken along line II-II in FIG. 1.

Further, from FIG. 2, it can be understood that the spring 3 also extends in an extension plane that closely connects to the outside of the foot in the area behind the ankle joint, i.e., between the ankle joint and the Achilles's tendon and that intersects the inner long edge of the footplate 2 at an angle of approx. 15° in the plane of the footplate.

The spring 3 comprises two spring strands 33, 34, which in the normal position of the spring lie approximately uniformly spaced-apart between the upper and lower end portions 31, 32 of the spring 3, in the extension plane of the spring 3. When the patient walks forward and his foot, which is in contact with the ground, moves rearward behind a vertical through the centre of gravity of the patient, the footplate 2 may swing upward around a fulcrum being defined by the spring 3 and coinciding with the axis 7 extending laterally of the leg.

When the foot then reaches the rear end position thereof, the user will turn down the foot and the footplate around the axis 7, and when the foot/footplate then leaves the ground for a forward motion in relation to the ground, the loaded spring 3 affords an upward swinging of the foot and the footplate in order to lift the foot.

By the design of the spring including two parallel curved spring strands 33, 34, a spring characteristic is afforded that increases the return force for the footplate 22, upon increased stride length or increased walking speed, so that the foot favourably is swung up quickly into the neutral position and is restrained from interfering with the ground.

On the other hand, the strands 33, 34 will come into contact with each other in the common extension plane thereof, when the footplate 22 and thereby the foot are swung up past the normal position, when the footplate 22 still abuts substantially parallel to the ground in the end part of the contact of the footplate 22 with the ground, whereby the spring 3 accordingly gets a particularly strong increase of the bending resistance thereof and thereby particularly well can compensate for weakness in the calf muscles of the user. Simply expressed, thanks to the structural design thereof, the spring 3 consequently affords different spring characteristic upon the bending of the footplate upward and downward, respectively, from the neutral position, in a good adaptation to the patient's needs.

From the drawing figures, it can be understood that the connecting element, i.e., the tongue 21 with the spring 3 and the lower part of the rail 4, extends close to the lower leg of the user at the same time as the connecting element affords a favorable springing function thanks to the design of the spring 3, the springing function producing a swinging motion between the upper and lower parts of the connecting element, the axis of which essentially coincides with the joint axis 7 of the patient's ankle joint. Furthermore, no interference arises between the connecting element and the adjacent ankle joint button 6. The patient having an orthosis fitted on puts down the foot together with the footplate 22 in his or her shoe, wherein the patient may have a foot sock either only on the foot or on the combination of the foot and footplate and spring 3, thereby efficiently concealing the orthosis.

By the fact that the spring extends along a curved path between the ends thereof, wherein the end portions mutually generally form a right angle, already from the beginning an increasing return force is attained for an increasing change of direction between the spring ends in the plane of the spring, starting from the unbiased state of the spring, at the same time as the spring affords different characteristic of deflection in opposite directions from the unbiased neutral state of the spring.

What is claimed is:

1. Below-knee orthosis comprising:
   a footplate; and
   a connecting element carrying the footplate and projecting therefrom, the connecting element including an upper end part which has a releasable coupling configured and operable to be coupled to an upper part of a patient's lower leg, the connecting element also including a longitudinal section having a spring element, the spring element having a fulcrum and extending in a curved path at a radial distance from the fulcrum the fulcrum of the spring element being placed to be substantially aligned with a patient's ankle-joint axis extending laterally of the patient's leg, the spring element further having two substantially parallel spring strands arranged at a mutual distance in a plane generally parallel to one of a lateral and a medial side of the patient's lower leg.

2. Below-knee orthosis according to claim 1, wherein the spring element extends behind the fulcrum of the spring element and extends in a surface that is substantially parallel to the one of the lateral and the medial side of the lower leg.

3. Below-knee orthosis according to claim 1, wherein the footplate is rigidly connected to the connecting element, and wherein the connecting element, with the exception of the spring element, is substantially rigid at a surface in which the spring element is deflected when the patient walks with the below-knee orthosis mounted.

4. Below-knee orthosis according to claim 1, wherein the entire connecting element extends along and in close proximity to the lower leg.

5. Below-knee orthosis according to claim 1, wherein the connecting element extends along an inside of the patient's lower leg.

\* \* \* \* \*